United States Patent [19]

Nore et al.

[11] Patent Number: 5,512,571
[45] Date of Patent: Apr. 30, 1996

[54] (-) [[4-(1,4,5,6-TETRAHYDRO-4-METHYL-6-OXO-3-PYRIDAZINYL)PHENYL]-HYDRAZONO]PROPANEDINITRILE

[75] Inventors: Pentti Nore, Helsinki; Erkki Honkanen, Espoo; Reijo Bäckström, Helsinki; Tom Wikberg; Heimo Haikala, both of Espoo; Jorma Haarala, Helsinki, all of Finland

[73] Assignee: Orion-yhtyma Oy, Espoo, Finland

[21] Appl. No.: 455,035

[22] Filed: May 31, 1995

Related U.S. Application Data

[62] Division of Ser. No. 81,360, Jun. 30, 1993, Pat. No. 5,424,428.

[30] Foreign Application Priority Data

Jan. 3, 1991 [GB] United Kingdom ............. 9100049
Sep. 5, 1991 [GB] United Kingdom ............. 9118947

[51] Int. Cl.$^6$ .................................................. C07D 37/14
[52] U.S. Cl. .................................................. 544/239
[58] Field of Search .................................................. 544/239

[56] References Cited

U.S. PATENT DOCUMENTS

| | | | |
|---|---|---|---|
| 4,521,415 | 6/1985 | Katakami et al. | 544/239 |
| 4,843,072 | 6/1989 | Yasuda et al. | 514/247 |
| 4,914,093 | 4/1990 | Morisawa et al. | 514/247 |
| 4,946,842 | 8/1990 | Coates et al. | 514/247 |
| 5,019,575 | 5/1991 | Haikala et al. | 514/247 |
| 5,151,420 | 9/1992 | Bäckström et al. | 514/247 |

FOREIGN PATENT DOCUMENTS

| | | |
|---|---|---|
| 0259835 | 6/1989 | European Pat. Off. . |
| 0208518 | 8/1990 | European Pat. Off. . |
| 2228004 | 5/1991 | United Kingdom . |
| 2251615 | 7/1992 | United Kingdom ............. 544/239 |
| WO92/12135 | 7/1992 | WIPO . |

OTHER PUBLICATIONS

*J. Org. Chem.* 1991, 56, 1963–1966, An Enantioselective synthesis of SK&F 93505, A Key Intermediate for Preparing Cardiotonic Agents by Franklin F. Owings, Margaret Fox, Conrad J. Kowalski, and Neil H. Baine.

"Synthesis and Biological Activity of Four Stereoisomers of 6–[4–[3–[[2[Hydroxy-3–[4–[2–(Cyclopropylmethoxy)ethyl]phenoxyl]propl]amino]–propionamide]phenyl]–5–methyl–4,5–dihydro–3(2H)–pyridazinone, a Combined Vasodilator and β–Adrenoceptor Antagonist", W. Howson et al., J. Med. Chem. 1988, vol. 31, pp. 352–356.

*Primary Examiner*—Ronald G. Daus
*Attorney, Agent, or Firm*—Burns, Doane, Swecker & Mathis

[57] ABSTRACT

Diastereomeric intermediate salts of formulae (IIIa) or (IIIb)

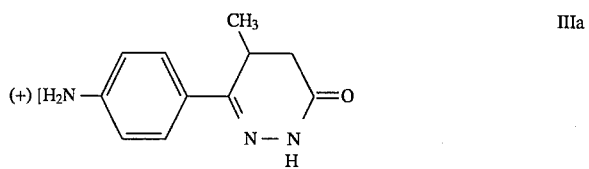

x L-tartaric acid x 2-propanol solvate],

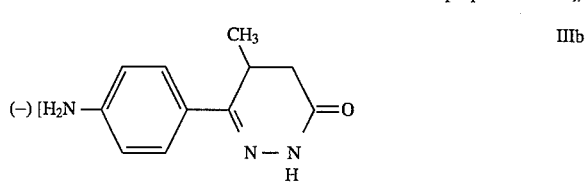

x L-tartaric acid x 2-propanol solvate], are prepared.

1 Claim, 1 Drawing Sheet

(-) [ [ 4-(1,4,5,6-TETRAHYDRO-4-METHYL-6-OXO-3-PYRIDAZINYL)PHENYL]-HYDRA-ZONO] PROPANEDINITRILE

This application is a divisional of application Ser. No. 08/081,360, filed Jun. 30, 1993 which is now U.S. Pat. No. 5,424,428 granted Jun. 13, 1995.

The present invention relates to the pure (−) enantiomer of [[4-(1,4,5,6-tetrahydro-4-methyl-6-oxo-3-pyridazinyl)phenyl]hydrazono]propanedinitrile of formula

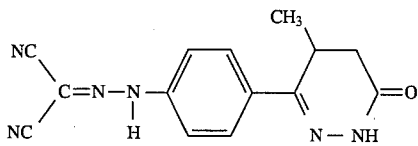

I

The invention also relates to salts, compositions and a process for the preparation of this enantiomer as well as to new intermediates of this process.

The compound according to the invention is useful as cardiotonic agent, antihypertensive and vasodilator for the treatment of congestive heart failure.

The racemic mixture of [[4-(1,4,5,6-tetrahydro-4-methyl-6-oxo-3-pyridazinyl)phenyl]hydrazono]propanedinitrile (I) with melting point of 258°–263° C. has been described earlier in applicants patent application GB 2228004. It was shown that the compound (I) is potent in the treatment of congestive heart failure and has significant calcium dependent binding to troponin. Our further studies have now unexpectedly revealed that the cardiotonic potency is predominantly due to the optically active (−) enantiomer of this compound. Furthermore it was found that the water solubility of the (−) enantiomer is over 30 fold compared to the racemate. The bioavailability of the (−) enantiomer was also found to be superior compared to racemate. Therefore the pure (−) enantiomer is especially suitable over the racemic compound to be used as a medicament for treating congestive heart failure.

The (+) and (−) enantiomers of [[4-(1,4,5,6-tetrahydro-4-methyl-6-oxo-3-pyridazinyl)phenyl]hydrazono]propanedinitrile (I) can be separated by passage of the racemic compound over a chiral phase chromatography column. However, this method is tedious if larger amounts of material is needed.

Another possibility to obtain the pure enantiomers of compound (I) is the use of corresponding optically active enantiomers of 6-(4-aminophenyl)-5-methylpyridazin-3(2H)one as an intermediate. The racemic 6-(4-amino-phenyl)-5-methyl-pyridazin-3(2H)one of formula (II)

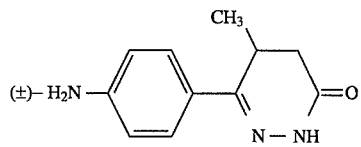

II can be synthesized by methods known in the literature (J. Med. Chem., 17, 273–281 (1974)). The resolution of the racemic compound (II) has, however, been proved very difficult because the 4-amino group in the molecule is weakly basic. The salts of 6-(4-amino-phenyl)-5-methylpyridazin-3(2H)one with optically active acids hydrolyse on crystallization readily back to the compound (II) and to the resolving compound which interfere the resolution procedure or make it totally impossible.

The separation of the pure enantiomers of compound (II) on a chiral HPLC-column has been described in European patent application EP 208518. This method is, however, not applicable for industrial scale. An enantioselective seven step synthesis of (−)-6-(4-aminophenyl)-5-methylpyridazin-3(2H)one starting from (+)-2-chloropropionic acid has also been described in the literature (J. Org. Chem., 56, 1963(1991)). The total yield in this method is only 12% giving (−)-6-(4-aminophenyl)-5-methylpyridazin-3(2H)one with an optical purity of 97.2%.

It was now found that good enantiomeric separation of compound (II) could be obtained by using L- or D-tartaric acid in excess, preferably about 2 to about 3 equivalents, to the compound (II) in 2-propanol. The acid salts of (−)-6(4-aminophenyl)-5-methylpyridazin-3(2H)one with L-tartaric acid 2-propanol solvate (IIIb) or corresponding (+)-6-(4-aminophenyl)-5-methylpyridazin-3(2H)one with D-tartaric acid 2-propanol solvate (IIIa) crystallize in good yield and in practical optical purity.

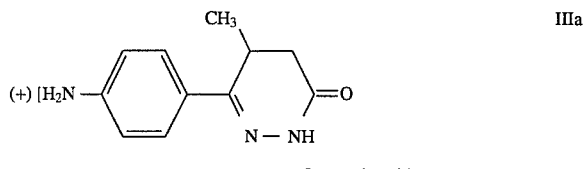

IIIa x L-tartaric acid x 2-propanol solvate]

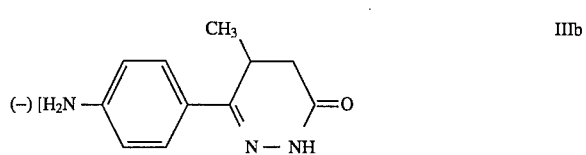

IIIb x L-tartaric acid x 2-propanol solvate]

It was further found that the minor component in a partly enriched enantiomer mixture may be crystallized out as racemic compound (II) from dioxane leaving the rest of the major component in the solution. Thus the salts (IIIa) or (IIIb) obtained in the crystallization mentioned above were filtered and the free base was liberated with potassium carbonate solution and the product were treated with dioxane. Both enantiomers of (I) are thus obtained by this two phase crystallization procedure in high optical purity of over 99%. The yield in this process is also very good, because the rasemic compound (I) is obtained from dioxane in crystalline state and may be recycled. Both resolving compounds L- or D-tartaric may be alternatively used in the above process, but the natural L-tartaric acid is preferable because it is much cheaper.

The optically substantially pure (−) and (+) enantiomers of the compound (I) may then be prepared from the corresponding optically substantially pure (−) and (+) enantiomer of compound (II), respectively, by the usual process disclosed in applicant's patent application GB 2228004, in high optical purity and in nearly quantitative yields. The process described in GB 2228004 for preparing the compound (I) comprises treating the compound of formula (II) with sodium nitrite and malononitrile in acidic conditions. The term "optically substantially pure" means here optical purity over about 90%, preferably over 95% and more preferably over 99%.

Salts of the enantiomers of compound (I) may be prepared by known methods. Pharmaceutically acceptable salts are useful as active medicaments, however, preferred are the salts with alkali or alkaline earth metals.

TABLE 1

The water solubility of (−) enantiomer and racemic mixture of [[4-(1,4,5,6-tetrahydro-4-methyl-6-oxo-3-pyridazinyl)phenyl]hydrazono]propanedinitrile (I) in 67 mM phosphate buffer (pH 2).

| Compound | Solubility (mg/ml) |
| --- | --- |
| (−) enantiomer | 0.029 |
| racemic | 0.0007 |

Cardiotonic action

Cardiotonic action of the (−) and (+) enantiomers of [[4-(1,4,5,6-tetrahydro-4-methyl-6-oxo-3-pyridazinyl)phenyl]hydrazono]propanedinitrile (I) was studied in isolated, electrically paced, right ventricular papillary muscle of guinea-pig. Experiments were carried out in normal Tyrode's bath solution as described by Otani et al., Japan. J. Pharmacol. 45, 425, 1987.

The results are presented in Table 2. They show that the (−) enantiomer was 47 times more potent than the (+) enantiomer.

TABLE 2

Cardiotonic effects of the (−) and (+) enantiomers of [[4-(1,4,5,6-tetra-hydro-4-methyl-6-oxo-3-pyridazinyl)phenyl]hydrazono]propanedinitrile in guinea-pig papillary muscle.

| Enantiomer | $EC_{50}$, mM |
| --- | --- |
| (−) | 0.06 |
| (+) | 2.8 |

Bioavailability

Figure 1:
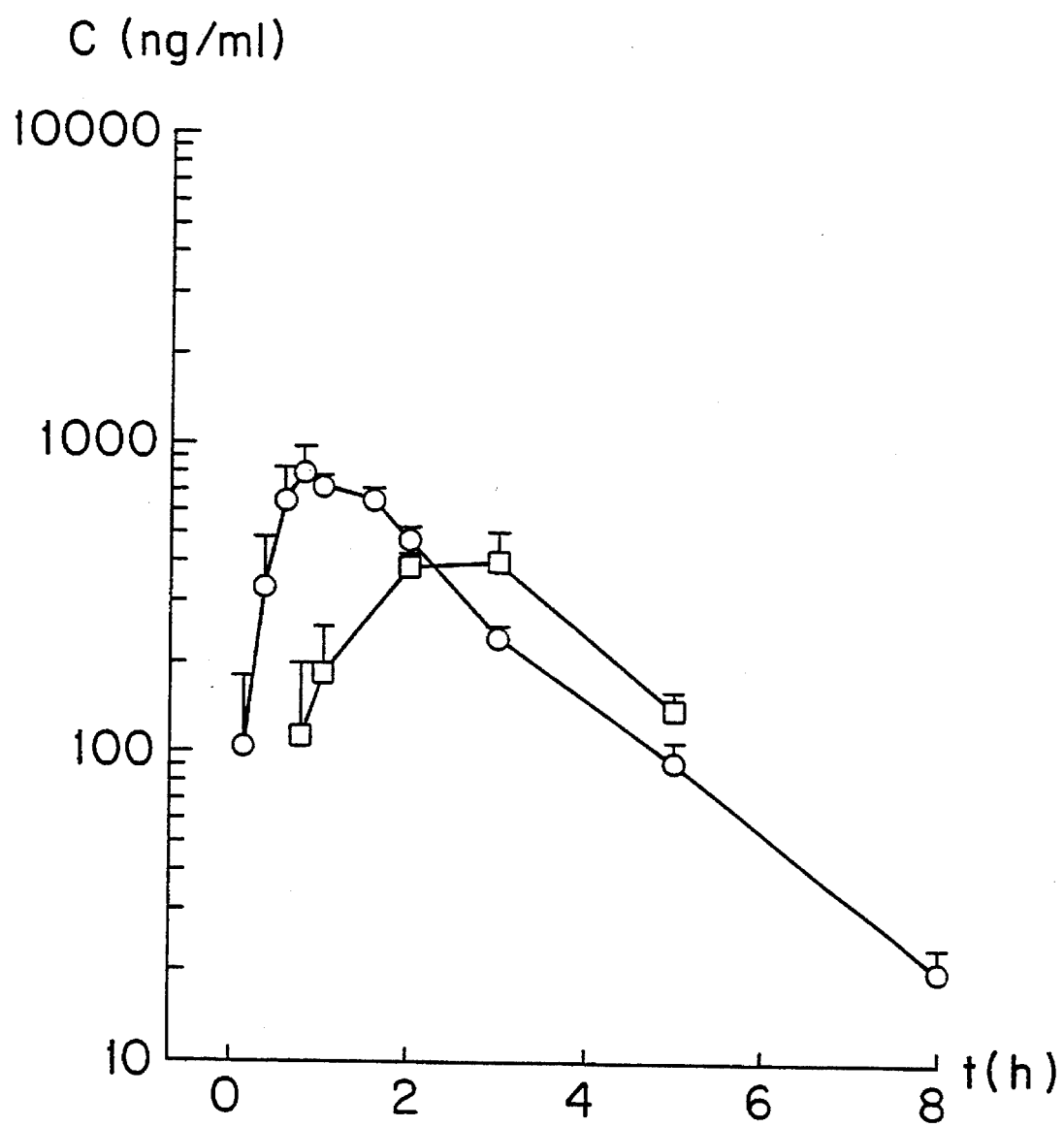
FIG. 1 is a graph depicting the concentration of total [[4-(1,4,5,6-tetrahydro-4-methyl-6-oxo-3-pyridazinyl)-phenyl]hydrazono]propanedinitrile in dog plasma over time after single dose oral administration of the racemate and the (−) enantiomer.

Concentration of total [[4-(1,4,5,6-tetrahydro-4-methyl-6-oxo-3-pyridazinyl)phenyl]hydrazono]propanedinitrile in dog plasma after single dose oral administration of the racemate (1 mg/kg) and (−)-enantiomer (0.5 mg/kg) is shown in FIG. 1. Curve A is for the (−)-enantiomer and curve B is for the racemic [[4-(1,4,5,6-tetrahydro-4-methyl-6-oxo-3-pyridazinyl)phenyl]hydrazono]propanedinitrile. The figure shows that when (−)-enantiomer is used instead of the racemate less than half dose is needed to produce the same plasma concentration level of the total drug substance.

The pharmaceutically active compound according to this invention is formulated into dosage form using the principles known in the art. It is given to mammalian organisms, i.e., humans, a patient as such or in combination with suitable pharmaceutical excipients in the form of tablets, dragees, capsules, suppositories, emulsions, suspensions or solutions. The composition according to the invention contains an therapeutically effective amount of the pharmaceutically active compound of the invention. The contents of the active compound is in the composition from about 0.5 to 100% per weight. In general, the compound of the invention may be administered to man in oral doses as low as ranging from about 1 to 50 mg per day. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The $LD_{50}$ value of the (−) enantiomer given intravenously to rats was 57 mg/kg.

The compositions are formulated depending upon the purpose of the medicine, normal uncoated tablets being quite satisfactory. Sometimes it is advisable to use coated tablets, i.e. so-called enterotablets, to secure that the medicine reaches the desired part of the gastrointestinal tract. Dragees and capsules may be used too.

EXAMPLE 1

Resolution of racemic 6-(4-aminophenyl)-5-methylpyridazin-3(2H)one with L-tartaric acid.

(±)-6-(4-aminophenyl)-5-methylpyridazin-3(2H)one (203 g, 1 mole) was dissolved in 2-propanol (40 dm³) on heating. To this solution (L)-tartaric acid (300 g, 2 mole) was gradually added. The mixture was stirred on heating until a clear solution was obtained. The solution was cooled slowly to room temperature with stirring. After it has been stirred over night at 20° C. the crystalline product (IIIb) was filtered. The wet salt was dissolved in water (1.5 dm³) and potassium carbonate solution (190 g $K_2CO_3$ in 0.75 dm³ of water) was added with stirring. The free base was filtered, washed with water and dried. The product (104.6 g) was dissolved in dioxane (0.6 dm³) on heating and allowed to cool to room temperature. The racemic 6-(4-aminophenyl)-5-methylpyridazin-3(2H)one was filtered (74.6g) and the filtrate was evaporated to dryness in vacuo yielding (−)-6-(4-aminophenyl)-5-methylpyridazin-3(2H)one as a crystalline solid (23.8 g) with optical purity of 99.5%, m.p. 207°–210° C., $[a]_D^{25}$=−383° (ethanol-water-conc. HCl 17:2:1).

The 2-propanol solution containing the (+)-enantiomer together with the racemate of compound (I) was evaporated to dryness in vacuo. The residue was treated with potassium carbonate solution as described above to give a mixture of (+)-enantiomer and racemate (87.3 g) which was dissolved on heating in dioxane (0.48 dm³). The racemate was filtrated after cooling (48.0 g) and the filtrate was evaporated to dryness in vacuo yielding (+)-6-(4-aminophenyl)-5-methylpyridazin-3(2H)one as a crystalline solid (26.1g) with optical purity of 99.5%, mp. 206°–209° C., $[a]_D^{25}$=+391° (ethanol-water-conc. HCl 17:2:1). In total 122.6 g of racemate was recovered. The yield of (−)-enantiomer of (I) was thus 59.2% and the yield of (+)-enantiomer of (I) 64.9%.

EXAMPLE 2.

(+)-[[4-(1,4,5,6-tetrahydro-4-methyl-6-oxo-3-pyridazinyl)phenyl]hydrazono]propanedinitrile The title compound was prepared as described in patent application GB 2228004 from (+)-6-(4-amino-phenyl)-5-methylpyridazin-3(2H)one. Yield 98%, mp 210–214° C., $[a]_D^{25}$=568° (tetrahydrofurane-methanol 1:1).

EXAMPLE 3.

(−)-[[4-(1,4,5,6-tetrahydro-4-methyl-6-oxo-3-pyridazinyl)phenyl]hydrazono]propanedinitrile The title compound was obtained as described above from (−)-6-(4-aminophenyl)-5-methylpyridazin-3(2H)one. Yield 97%, mp 210°–214° C., $[a]_D^2$=−566° (tetrahydrofurane-methanol 1:1).

EXAMPLE 4.

Preparation of pure diastereomeric salt (IIIa)

508 mg (2.5 mmol) of pure (+)-6-(4-aminophenyl)-5-methylpyridazin-3(2H)one obtained in Example 1 was dissolved in 100 ml of 2-propanol. 750 mg (5.0 mmol) of D-tartaric acid was added and the mixture was heated to boiling. On cooling 800 mg of crystalline (+)-6-(4-aminophenyl)5-methyl-pyridazin-3(2H)one D-tartrate mono 2-propanol solvate was obtained, mp. 97°–105°C.

EXAMPLE 5.

Preparation of pure diastereomeric salt (IIIb)

The above process was repeated by using (−)-6-(4-aminophenyl)-5-methylpyridazin-3(2H)one and L-tartaric acid. Mp. 98°–106° C.

EXAMPLE 6.

Preparation of (−)-6-(4-aminophenyl)-5-methylpyridazin-3(2H)one by resolution of the corresponding racemate with L-tartaric acid.

(±)-6-(4-aminophenyl)-5-methylpyridazin-3(2H)one (203 g, 1 mole)was dissolved in 2-propanol (10 dm$^3$) on heating. To this solution (L)-tartaric acid (300 g, 2 mole) was gradually added. The mixture was stirred on heating until a clear solution was obtained and cooled slowly during 3 h to 50° C. and stirred further over night at 50° C. The crystalline product was filtered and the procedure described in Example 1 was repeated. The yield of (−)-6-(4-aminophenyl)-5-methylpyridazin-3(2H)one was 30.3 g (97.4% of the theoretical). The optical purity was 99.7%. In total 140.8 g of the racemate was recovered.

The optical purities of the compounds were determined by the high performance liquid chromatography. The instrument was a Waters 600 E gradient pump with a Waters 991 photodiode array detector and a Waters 700 Satellite Wisp injector (Millipore Co.) controlled by a NEC Powermate SX Plus computer. The enantiomers of 6-(4-aminophenyl)-5-methylpyridazin-3(2H)one were separated by using a sellulose-type chiral column (Chiracel=OJ, 4.6×250 mm, Daicel Chemical Industries LTD.). The mobile phase consisted of 97% 2-propanol and 3% hexane. The flow rate was 0.3 ml/min. The enantiomers of [[4-(1,4,5,6-tetrahydro-4-methyl-6-oxo-3-pyridazinyl)phenyl]hydrazono]propanedinitrile were separated by using a β-cyclodextrin column (Cyclobond lb, 4.6×250 mm, Advance Separation Technologies Inc.). The mobile phase consisted of 41% methanol in water buffered to pH 4.0 with 1% triethylammonium acetate. The flow rate was 0.3 ml/min.

We claim:

1. Diastereomeric intermediate salts of formulae (IIIa) or (IIIb)

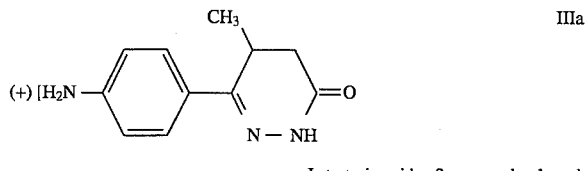

x L-tartaric acid x 2-propanol solvate]

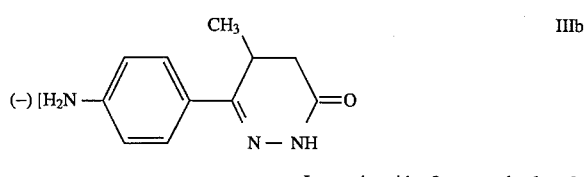

x L-tartaric acid x 2-propanol solvate].

* * * * *

UNITED STATES PATENT AND TRADEMARK OFFICE
CERTIFICATE OF CORRECTION

PATENT NO. : 5,512,571

DATED : April 30, 1996

INVENTOR(S) : PENTTI NORE et al.

It is certified that error appears in the above-indentified patent and that said Letters Patent is hereby corrected as shown below:

On the title page, item [56], and column 1:

--6-(4 Amino phenyl) 5 Methyl pyridazin-3(2H) one-L-Tartaric Salt 2 Propanol Solvates--.

Please amend the Abstract as follows:

At IIIa, please delete "L-tartaric acid" and insert --D-tartaric acid--.

At Column 2, line 25, please delete "L-tartaric acid" and insert --D-tartaric acid--.

At Column 3, line 28, please delete "mM" and insert --$\mu$M--.

At Column 6, line 26, Claim 1, please delete "L-tartaric acid" and insert --D-tartaric acid--.

UNITED STATES PATENT AND TRADEMARK OFFICE
CERTIFICATE OF CORRECTION

PATENT NO. : 5,512,571

DATED : April 30, 1996

INVENTOR(S) : PENTTI NORE et al.

It is certified that error appears in the above-indentified patent and that said Letters Patent is hereby corrected as shown below:

At Column 6, line 26, Claim 1, please delete "L-tartaric acid" and insert --D-tartaric acid--.

Signed and Sealed this

Fifth Day of November, 1996

Attest:

BRUCE LEHMAN

*Attesting Officer*     *Commissioner of Patents and Trademarks*